US012797323B2

(12) United States Patent
Suthiwangcharoen et al.

(10) Patent No.: US 12,797,323 B2
(45) **Date of Patent: *Nov. 17, 2026**

(54) PROCESS FOR REDUCING HAIR DAMAGE UPON EXPOSURE TO HEAT

(71) Applicants: Dow Global Technologies LLC, Midland, MI (US); Dow Silicones Corporation, Midland, MI (US); Rohm and Haas Company, Collegeville, PA (US)

(72) Inventors: Nisaraporn Suthiwangcharoen, Midland, MI (US); Justin Scherzer, Freeland, MI (US); Victoria Walsh, Saginaw, MI (US); Shannon Golden, Saginaw, MI (US); Emmett M. Partain, III, Bound Brook, NJ (US); Lyndsay M. Leal, Spring City, PA (US); Jennifer P. Todd, Willow Grove, PA (US)

(73) Assignees: Dow Global Technologies LLC, Midland, MI (US); Dow Silicones Corporation, Midland, MI (US); Rohm and Haas Company, Collegeville, PA (US)

( * ) Notice: Subject to any disclaimer, the term of this patent is extended or adjusted under 35 U.S.C. 154(b) by 397 days.

This patent is subject to a terminal disclaimer.

(21) Appl. No.: 18/261,509

(22) PCT Filed: Mar. 9, 2022

(86) PCT No.: PCT/US2022/019468

§ 371 (c)(1),
(2) Date: Jul. 14, 2023

(87) PCT Pub. No.: WO2022/203864

PCT Pub. Date: Sep. 29, 2022

(65) Prior Publication Data

US 2024/0307287 A1 Sep. 19, 2024

Related U.S. Application Data

(60) Provisional application No. 63/164,061, filed on Mar. 22, 2021.

(51) Int. Cl.

*A61K 8/73* (2006.01)
*A45D 19/00* (2006.01)
*A61Q 5/00* (2006.01)

(52) U.S. Cl.

CPC ............ *A61K 8/73* (2013.01); *A45D 19/0041* (2021.01); *A61Q 5/002* (2013.01); *A61K 2800/5426* (2013.01)

(58) Field of Classification Search

CPC .............. A61K 8/73; A61K 2800/5426; A61K 2800/24; A61K 2800/57; A61K 2800/48; A61K 2800/51; A61K 2800/524; A45D 19/0041; A61Q 5/002

See application file for complete search history.

(56) References Cited

U.S. PATENT DOCUMENTS

| | | | | |
|---|---|---|---|---|
| 4,411,891 | A | 10/1983 | Mizutani et al. | |
| 8,518,387 | B2 | 8/2013 | Drovetskaya et al. | |
| 10,633,683 | B2 | 4/2020 | Paullin et al. | |
| 10,716,748 | B2 | 7/2020 | Gonzalez et al. | |
| 10,874,598 | B2 | 12/2020 | Yang et al. | |
| 2008/0003192 | A1 | 1/2008 | Modi | |
| 2010/0093584 | A1 * | 4/2010 | Brand .................. | A61K 8/736 510/159 |
| 2010/0247472 | A1 | 9/2010 | Sau | |
| 2011/0177017 | A1 | 7/2011 | Coffindaffer et al. | |

(Continued)

FOREIGN PATENT DOCUMENTS

| | | |
|---|---|---|
| CN | 106511133 | 3/2017 |
| DE | 10018158 | 10/2001 |

(Continued)

OTHER PUBLICATIONS

Profashion (How hot is too hot?) Accessed: Oct. 9, 2025 (Year: 2025).*

Watson (Healthline, How to Treat Heat-Damaged Hair Without Cutting It, Sep. 23, 2019) (Year: 2019).*

Profashion (How hot is too hot?, Accessed May 12, 2026) (Year: 2026).*

Watson (Healthline, Sep. 23, 2019) (Year: 2019).*

Pawar et al. (Natural-Based Polymers for Biomedical Applications, 2008, pp. 3-53) (Year: 2008).*

(Continued)

*Primary Examiner* — Sahana S Kaup
*Assistant Examiner* — Abdulrahman Abbas
(74) *Attorney, Agent, or Firm* — Thomas S. Deibert

(57) ABSTRACT

A process for reducing hair damage upon exposure to heat is provided, including: providing a cosmetically acceptable aqueous carrier: selecting a heat protectant, wherein the heat protectant is selected based on its ability to impart thermal protection to hair from exposure to heat, wherein the heat protectant is selected to be a functionalized dextran polymer, comprising a dextran polymer functionalized with moieties selected from (i) tertiary amine groups: (ii) quaternary ammonium groups; and (iii) combinations thereof; providing the selected heat protectant; combining the cosmetically acceptable aqueous carrier and the heat protectant to form an aqueous thermal protectant formulation; providing hair; applying the aqueous thermal protectant formulation to the hair to provide protected hair; providing a heat generating hair care appliance; and exposing the protected hair to a temperature of 50 to 300 C using the heat generating hair care appliance for 1 to 30 minutes.

11 Claims, No Drawings

(56) References Cited

U.S. PATENT DOCUMENTS

| | | | | |
|---|---|---|---|---|
| 2015/0034117 | A1* | 2/2015 | Pressly | A61K 8/362 424/70.2 |
| 2015/0098920 | A1 | 4/2015 | Stella et al. | |
| 2015/0203598 | A1 | 7/2015 | Landschutze et al. | |
| 2018/0237816 | A1 | 8/2018 | Paullin et al. | |

FOREIGN PATENT DOCUMENTS

| | | | |
|---|---|---|---|
| EP | 2119428 | | 11/2009 |
| EP | 3486356 | | 5/2019 |
| JP | 10279449 | | 10/1998 |
| JP | 11322555 | | 11/1999 |
| JP | 2000159642 | | 6/2000 |
| JP | 2000319139 | | 11/2000 |
| JP | 2000319139 | A * | 11/2000 |
| JP | 3720964 | | 11/2005 |
| JP | 2009062281 | | 3/2009 |
| JP | 4712222 | | 6/2011 |
| WO | 2010009938 | | 1/2010 |
| WO | 2010089228 | | 8/2010 |
| WO | 2014047099 | | 3/2014 |
| WO | 2017174678 | | 10/2017 |
| WO | 2021194804 | | 9/2021 |
| WO | 2021194805 | | 9/2021 |
| WO | 2021194807 | | 9/2021 |
| WO | 2021194809 | | 9/2021 |

OTHER PUBLICATIONS

Mintel, "Chinese Medicine Anti-Dandruff & Olive Moisturising Shampoo", Bawang Cosmetic, 2015, Database GNPD, CN.

Mintel, "Refresh Mint Cool Body Wash Gel", Bawang Cosmetic, 2015, Database GNPD, CN.

Sibilia "A Guide to Materials Characterization and Chemical Analysis", VCH, 1988, pp. 81-84.

Stanciu "Influence of dextran hydrogel characteristics on adsorption capacity for anionic dyes", Carbohydrate Polymers, 2018, vol. 199, pp. 75-83, Applied Science Publishers, Ltd., Barking, GB.

Yau, "Modern Size Exclusion Chromatography", 1979, Wiley-Interscience.

* cited by examiner

PROCESS FOR REDUCING HAIR DAMAGE UPON EXPOSURE TO HEAT

The present invention relates to a process for reducing hair damage upon exposure of the hair to heat. In particular, the present invention relates to a process for reducing hair damage upon exposure of the hair to heat, comprising: providing a cosmetically acceptable aqueous carrier; selecting a heat protectant, wherein the heat protectant is selected based on its ability to impart thermal protection to hair from exposure to heat, wherein the heat protectant is selected to be a functionalized dextran polymer, comprising a dextran polymer functionalized with moieties selected from the group consisting of (i) tertiary amine groups; (ii) quaternary ammonium groups; and (iii) combinations thereof; providing the selected heat protectant; combining the cosmetically acceptable aqueous carrier and the heat protectant to form an aqueous thermal protectant formulation; providing a hair; applying the aqueous thermal protectant formulation to the hair to provide a protected hair; providing a heat generating hair care appliance; and exposing the protected hair to a temperature of 50 to 300 °C using the heat generating hair care appliance for 1 to 30 minutes.

Heat-assisted processes whereby heat is applied to hair fibers (e.g., during heat-assisted styling or drying using blow dryers, hair straighteners (such as flat irons), curling devices, heated comb, heated brush (with or without a rotating drum) are ubiquitous. Such heat-assisted processes; however, can dry out and damage hair. Moreover, improper technique may lead to damager; such as, for example, holding a blow dryer too close to the hair and overdrying the hair, or by engaging hair with a hot tool for too long at a particular spot of the hair. The heat assisted processes may cause moisture to evaporate or be driven from the hair causing the hair to become brittle and more susceptible to cracking. In addition, heat styling may cause physical damage to the hair. For example, by raising the cuticles and/or creating blisters on individual hair fibers, which may lead to causing increased friction between hair fibers. The increased friction between hair fibers make combing more difficult requiring more force to comb through the hair. The application of increased combing force may in turn wear the outer surface of the hair leading to cracks and breaks in the hair. For many years, researchers believed that human hair would have similar temperature based properties to wool as both are composed of the keratin protein. Recent studies have revealed that human hair exhibits the following characteristics in response to heating. (a) When exposed to heat at ≤150 °C, loosely bound water and tightly bound water is lost or evaporated from the human hair. (b) When exposed to heat at 160 °C to 175 °C, human hair undergoes a glass transition phase; wherein the hair begins to flow as would hot glass. At the glass transition temperature hair may undergo plastic deformation. Normally hydrated hair may elastically stretch and return back to its original length. Hence, normally hydrated hair exhibits temporary plasticity which is why styles like curls, and twist outs/knot outs can occur. However, when treated above the glass transition temperature, the plasticity of hair is not temporary. Upon cooling, the hair may retain the styled, but the hair shaft will have been damaged. (c) When exposed to heat at 215 °C to 235 °C, the keratin, which is present in all hair as a natural alpha helix, melts, thereby permanently damaging the hair. Note that styling of hair is typically done using tools that exhibit operating temperatures in excess of 150 °C to impart style to the hair above the glass transition. When using heat to style hair, the temperature required to exceed the glass transition temperature is proportional to the hydration level of the hair. The higher the moisture content of the hair, the lower the temperature required to reach the glass transition point for the hair. Accordingly, to result in the lowest possible level of undesired damage to the hair, it would be advantageous to maximize the hydration of the hair during the heat assisted styling process.

One process for treating keratin fibers is described by Greaves al. in WO 2019043032. Greaves et al. disclose a process for treating keratin fibers, especially human keratin fibers, in particular the hair, comprising: (i) a step consisting in applying, to said fibers, a) one or more monosaccharides with amine group(s); (ii) a step consisting in applying, to said fibers, b) one or more polysaccharides with amine group(s); (ii') optionally a drying step; (iii) then a step of heat treatment at a temperature above or equal to 80 °C, in particular at a temperature between 100 °C and 250 °C, preferably with a hair iron; it being understood that the steps (i) and (ii) may be carried out simultaneously, or sequentially, preferably the steps (i) and (ii) are carried out simultaneously and that the drying step (ii'), when it is present, precedes the heat treatment step and follows the steps (i) and (ii).

Notwithstanding, there remains a need for processes for reducing hair damage upon exposure of heat to the hair.

The present invention provides a process for reducing hair damage upon exposure of the hair to heat, comprising: providing a cosmetically acceptable aqueous carrier; selecting a heat protectant, wherein the heat protectant is selected based on its ability to impart thermal protection to hair from exposure to heat, wherein the heat protectant is selected to be a functionalized dextran polymer, comprising a dextran polymer functionalized with moieties selected from the group consisting of (i) tertiary amine groups; (ii) quaternary ammonium groups; and (iii) combinations thereof; providing the selected heat protectant; combining the cosmetically acceptable aqueous carrier and the heat protectant to form an aqueous thermal protectant formulation; providing a hair; applying the aqueous thermal protectant formulation to the hair to provide protected hair; providing a heat generating hair care appliance; and exposing the protected hair to a temperature of 50 to 300 °C using the heat generating hair care appliance for 1 to 30 minutes.

The present invention provides a process for reducing hair damage upon exposure of the hair to heat, comprising: providing a cosmetically acceptable aqueous carrier; selecting a heat protectant, wherein the heat protectant is selected based on its ability to impart thermal protection to hair from exposure to heat, wherein the heat protectant is selected to be a functionalized dextran polymer, comprising a dextran polymer functionalized with moieties selected from the group consisting of (a) tertiary amine groups of formula A (A)

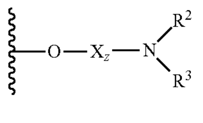

(b) quaternary ammonium crosslinking groups of formula B (B)

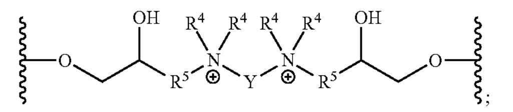

(c) quaternary ammonium groups of formula C (C)

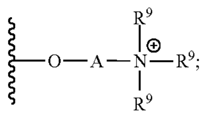

and (d) combinations thereof; wherein

is a pendant oxygen on the dextran polymer; wherein X is a divalent linking group bonding the tertiary amine group to the pendent oxygen; wherein z is 0 or 1; wherein $R^2$ and $R^3$ are independently selected from the group consisting of a $C_{1-7}$ alkyl group; wherein each $R^4$ is independently selected from a substituted or unsubstituted $C_{1-6}$ alkyl group; wherein each $R^5$ is independently selected from the group consisting of a $C_{1-6}$ alkanediyl group; wherein Y is a divalent bridging group; wherein A is a divalent linking group bonding the quaternary ammonium group to the pendent oxygen; wherein each $R^9$ is independently selected from the group consisting of a $C_{1-22}$ alkyl group; providing the selected heat protectant; combining the cosmetically acceptable aqueous carrier and the heat protectant to form an aqueous thermal protectant formulation; wherein the aqueous thermal protectant formulation contains 0.1 to 5 wt %, based on weight of the aqueous thermal protectant formulation, of the heat protectant; providing a hair; applying the aqueous thermal protectant formulation to the hair to provide protected hair; providing a heat generating hair care appliance; and exposing the protected hair to a temperature of 50 to 300 °C using the heat generating hair care appliance for 1 to 30 minutes.

DETAILED DESCRIPTION

We have surprisingly found that hair treated with an aqueous thermal protectant formulation of the present invention before exposure to heat; wherein the aqueous thermal protection formulation includes a selected heat protectant, wherein the heat protectant is selected based on its ability to impart thermal protection to hair from exposure to heat, wherein the heat protectant is selected to be a functionalized dextran polymer, comprising a dextran polymer functionalized with moieties selected from the group consisting of (i) tertiary amine groups; (ii) quaternary ammonium groups; and (iii) combinations thereof; the treated hair exhibits at least one of a higher denaturation temperature than hair similarly exposed to heat but without application of the aqueous protectant formulation (as measured using differential scanning calorimetry) and a higher denaturation enthalpy than hair similarly exposed to heat but without application of the aqueous protectant formulation (as measured using differential scanning calorimetry).

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and conventional standards, such as polyethylene glycol standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons, or equivalently, g/mol.

The term "cosmetically acceptable" as used herein and in the appended claims refers to ingredients typically used in personal care compositions, and is intended to underscore that materials that are toxic when present in the amounts typically found in personal care compositions are not contemplated as part of the present invention.

Preferably, the process for reducing hair (preferably, mammalian hair; more preferably, human hair) damage upon exposure of the hair to heat of the present invention, comprises: providing a cosmetically acceptable aqueous carrier; selecting a heat protectant, wherein the heat protectant is selected based on its ability to impart thermal protection to hair from exposure to heat, wherein the heat protectant is selected to be a functionalized dextran polymer, comprising a dextran polymer functionalized with moieties selected from the group consisting of (i) tertiary amine groups; (ii) quaternary ammonium groups; and (iii) combinations thereof; providing the selected heat protectant; combining the cosmetically acceptable aqueous carrier and the heat protectant to form an aqueous thermal protectant formulation; (preferably, wherein the aqueous thermal protectant formulation comprises 25 to 99.95 wt % (preferably, 50 to 99.9 wt %; more preferably, 75 to 99.5 wt %; most preferably, 80 to 99.3 wt %), based on weight of the aqueous thermal protectant formulation, of the cosmetically acceptable aqueous carrier; and 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of the heat protectant); providing a hair; applying the aqueous thermal protectant formulation to the hair to provide protected hair (preferably, applying from 0.01 g to 5 g of the aqueous hair care formulation per g of hair); optionally, rinsing the hair with water (preferably, wherein the hair is rinsed before applying the aqueous protectant formulation to the hair); optionally, drying the rinsed hair by at least one of toweling and pressing hair to remove excess water (preferably, wherein the hair is dried by at least one of toweling and pressing hair to remove excess water before applying the aqueous protectant formulation to the hair); optionally, at least one of combing and brushing the hair following application of the aqueous thermal protectant formulation (preferably, wherein the hair is combed and/or brushed before, during and/or after exposing the hair to heat from the heat generating hair care appliance); providing a heat generating hair care appliance (e.g., flat ironing/curling; setting hair in curlers and heating; curling with a curling iron; and hot rollers)(a hair styling appliance, wherein the hair styling appliance is selected from the group consisting of at least one of a hair dryer, a hot air hair styler and a hair curler); and exposing the protected hair to a temperature of 50 to 300 °C (preferably, 80 to 280 °C; more preferably, 90 to 275 °C; most preferably, 100 to 250 °C) using the heat generating hair care appliance (preferably, wherein the heat generating hair care appliance is selected from the group consisting of at least one of a hot air hair care appliance (e.g., hair dryer, hot air hair styler) and a hot surface hair care appliance (e.g., hot curlers, flat iron and a curling iron)) for 1 to 30 minutes (e.g., for drying or styling hair) (preferably, providing a hot air hair care appliance and a hot surface hair care appliance for 1 to 20 minutes for drying the hair followed by treatment of the hair with a hot surface hair care appliance for 1 to 20 minutes for styling the hair)(preferably, wherein the hair to which the aqueous protectant formulation has been applied exhibits at least one of a higher denaturation temperature than hair similarly exposed to heat but without application of the aqueous protectant formulation and a higher denaturation enthalpy than hair similarly exposed to heat but without application of the aqueous protectant formulation)(more preferably, wherein the hair to which the aqueous protectant formulation has been applied exhibits a higher denaturation temperature and a higher denaturation enthalpy than hair similarly exposed to heat but without application of the aqueous protectant formulation).

Preferably, the aqueous thermal protectant formulation prepared and used in the process of the present invention, comprises 25 to 99.95 wt % (preferably, 50 to 99.9 wt %; more preferably, 75 to 99.5 wt %; most preferably, 80 to 99.3 wt %), based on weight of the aqueous thermal protectant formulation, of a cosmetically acceptable aqueous carrier. More preferably, the aqueous thermal protectant formulation provided and used in the process of the present invention, comprises: 25 to 99.95 wt % (preferably, 50 to 99.9 wt %; more preferably, 75 to 99.5 wt %; most preferably, 80 to 99.3 wt %), based on weight of the aqueous thermal protectant formulation, of a cosmetically acceptable aqueous carrier; wherein the cosmetically acceptable aqueous carrier comprises water. Most preferably, the aqueous conditioner formulation of the present invention, comprises: 25 to 99.95 wt % (preferably, 50 to 99.9 wt %; more preferably, 75 to 99.5 wt %; most preferably, 80 to 99.3 wt %), based on weight of the aqueous thermal protectant formulation, of the cosmetically acceptable aqueous carrier; wherein the cosmetically acceptable carrier is water.

Preferably, the water used in the aqueous thermal protectant formulation prepared and used in the process of the present invention is at least one of distilled water and deionized water. More preferably, the water used in the aqueous thermal protectant formulation prepared and used in the process of the present invention is distilled and deionized.

Preferably, the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant. More preferably, the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected to impart thermal protection to hair from exposure to heat and wherein the heat protectant is selected to be a functionalized dextran polymer, comprising a dextran polymer functionalized with moieties selected from the group consisting of (i) tertiary amine groups; (ii) quaternary ammonium groups; and (iii) combinations thereof.

Preferably, the heat protectant is selected to be a dextran polymer functionalized with moieties selected from the group consisting of (i) tertiary amine groups; (ii) quaternary ammonium groups; and (iii) combinations thereof; wherein the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons). More preferably, the heat protectant is selected to be a dextran polymer functionalized with a moieties selected from the group consisting of (i) tertiary amine groups; (ii) quaternary ammonium groups; and (iii) combinations thereof; wherein the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons) and wherein the dextran polymer is a branched chain dextran polymer. Still more preferably, the heat protectant is selected to be a dextran polymer functionalized with a moieties selected from the group consisting of (i) tertiary amine groups; (ii) quaternary ammonium groups; and (iii) combinations thereof; wherein the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons); wherein the dextran polymer comprises a branched chain dextran polymer; wherein the branched chain dextran polymer comprises a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages. Most preferably, the heat protectant is selected to be a dextran polymer functionalized with moieties selected from the group consisting of (i) tertiary amine groups; (ii) quaternary ammonium groups; and (iii) combinations thereof; wherein the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons); wherein the dextran polymer is a branched chain dextran polymer; wherein the branched chain dextran polymer comprises a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages according to formula (i)

(i)

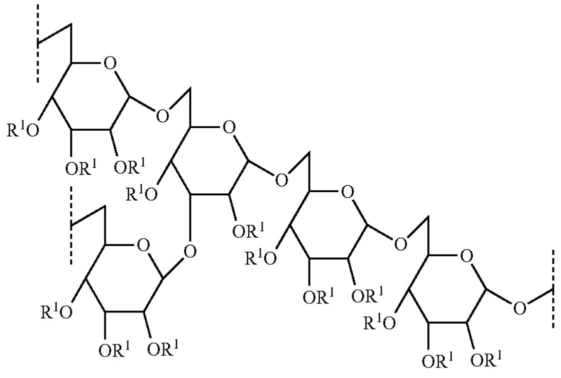

wherein $R^1$ is selected from a hydrogen, a $C_{1-4}$ alkyl group and a hydroxy $C_{1-4}$ alkyl group; and wherein the average branch off the dextran polymer backbone is ≤3 anhydroglucose units.

Preferably, the dextran polymer contain less than 0.01 wt %, based on weight of the dextran polymer, of alternan. More preferably, the dextran polymer contain less than 0.001 wt %, based on weight of the dextran polymer, of alternan. Most preferably, the dextran polymer contain less than the detectable limit of alternan.

Preferably, the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected to impart thermal protection to hair from exposure to heat and wherein the heat protectant is selected to be a functionalized dextran polymer, comprising a dextran polymer functionalized with moieties selected from the group consisting of (a) tertiary amine groups of formula A (A)

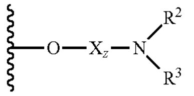

(b) quaternary ammonium crosslinking groups of formula B (B)

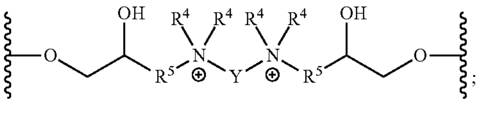

(c) quaternary ammonium groups of formula C (C)

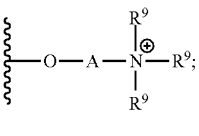

and (d) combinations thereof; wherein

is a pendant oxygen on the dextran polymer; wherein X is a divalent linking group bonding the trialkyl ammonium moiety to the pendent oxygen on the branched chain dextran polymer (preferably, wherein X is selected from divalent hydrocarbon groups, which may optionally be substituted (e.g., with a hydroxy group, an alkoxy group, an ether group, a cationic nitrogen group); more preferably, wherein X is a $—(CH_2)_y—$ group, wherein y is 1 to 4 (preferably, 1 to 3; more preferably, 1 to 2; most preferably, 2); most preferably, X is a $—CH_2CH_2—$ group); wherein z is 0 or 1; wherein $R^2$ and $R^3$ are independently selected from the group consisting of a $C_{1-7}$ alkyl group (preferably, a $C_{1-3}$ alkyl group; more preferably, a methyl group and an ethyl group; most preferably, an ethyl group) or $R^2$ and $R^3$ may form a saturated or unsaturated ring structure (preferably, wherein the saturated or unsaturated ring structure including the N from which $R^2$ and $R^3$ are bound is selected from the group consisting of piperidine, piperazine, imidazole and morpholine; more preferably, wherein the saturated or unsaturated ring structure including the N from which $R^2$ and $R^3$ are bound is selected from the group consisting of imidazole and morpholine); wherein each $R^4$ is independently selected from a substituted or unsubstituted $C_{1-6}$ alkyl group (wherein "substituted" means that the group in question contains at least one of a halogen, a hydroxy group, an amino group or a carboxy group) (preferably, wherein each $R^4$ is independently selected from an unsubstituted $C_{1-6}$ alkyl group; more preferably, wherein each $R^4$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^4$ is independently selected from the group consisting of a methyl group, an ethyl group, a propyl group, an isopropyl group, a butyl group, an isobutyl group, a tert-butyl group and a sec-butyl group; yet more preferably, wherein each $R^4$ is independently selected from the group consisting of a methyl group, an ethyl group, a propyl group and an isopropyl group; yet still more preferably, wherein each $R^4$ is independently selected from the group consisting of a methyl group and an ethyl group; most preferably, wherein each $R^4$ is a methyl group); wherein each $R^5$ is independently selected from the group consisting of a $C_{1-6}$ alkanediyl group (preferably, wherein each $R^5$ is independently selected from the group consisting of a $C_{1-4}$ alkanediyl group; more preferably, wherein each $R^5$ is independently selected from the group consisting of a $C_{1-2}$ alkanediyl group; most preferably, wherein each $R^5$ is a $—CH_2—$ group); wherein Y is a divalent bridging group (preferably, wherein Y is a divalent bridging group selected from the group consisting of a $C_{1-6}$ alkanediyl group and a $—R^6—O—R^1—$ group; more preferably, wherein Y is a $—R^6—O—R^7—$ group); wherein $R^6$ and $R^7$ are independently selected from the group consisting of a $C_{1-6}$ alkanediyl group (preferably, wherein $R^6$ and $R^7$ are independently selected from the group consisting of a $C_{1-4}$ alkanediyl group; more preferably, wherein $R^6$ and $R^7$ are independently selected from the group consisting of a $C_{1-3}$ alkanediyl group; most preferably, wherein $R^6$ and $R^7$ are both a —$CH_2CH_2$— group)(preferably, wherein $R^6$ and $R^7$ are the same); wherein A is a divalent linking group bonding the quaternary ammonium moiety to the pendent oxygen on the dextran polymer (preferably, wherein A is selected from divalent hydrocarbon groups, which may optionally be substituted (e.g., with a hydroxy group, an alkoxy group, an ether group); more preferably, wherein A is a —$CH_2CH(OR^8)CH_2$— group, wherein $R^8$ is selected from the group consisting of a hydrogen and a $C_{1-4}$ alkyl group; most preferably, wherein A is a —$CH_2CH(OH)CH_2$— group); and wherein each $R^9$ is independently selected from the group consisting of a $C_{1-22}$ alkyl group. More preferably, the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected to impart thermal protection to hair from exposure to heat and wherein the heat protectant is selected to be a functionalized dextran polymer, comprising a dextran polymer functionalized with moieties selected from the group consisting of (a) tertiary amine groups of formula A; (b) quaternary ammonium crosslinking groups of formula B; (c) quaternary ammonium groups of formula C; and (d) combinations thereof; wherein the quaternary ammonium crosslinking groups of formula B are of formula D (D)

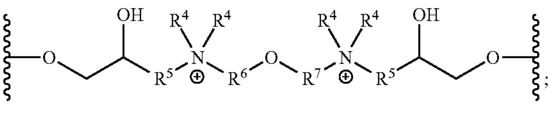

wherein the quaternary ammonium groups of formula Care of formula E (E)

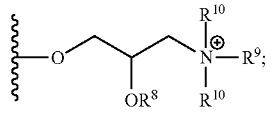

wherein

is a pendant oxygen on the dextran polymer; wherein each $R^4$ is independently selected from a substituted or unsubstituted $C_{1-6}$ alkyl group (preferably, wherein each $R^4$ is independently selected from an unsubstituted $C_{1-6}$ alkyl group; more preferably, wherein each $R^4$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^4$ is independently selected from the group consisting of a methyl group, an ethyl group, a propyl group, an isopropyl group, a butyl group, an isobutyl group, a tert-butyl group and a sec-butyl group; yet more preferably, wherein each $R^4$ is independently selected from the group consisting of a methyl group, an ethyl group, a propyl group and an isopropyl group; yet still more preferably, wherein each $R^4$ is independently selected from the group consisting of a methyl group and an ethyl group; most preferably, wherein each $R^4$ is a methyl group); wherein each $R^5$ is independently selected from the group consisting of a $C_{1-6}$ alkanediyl group (preferably, wherein each $R^5$ is a $C_{1-4}$ alkanediyl group; more preferably, wherein each $R^5$ is a $C_{1-2}$ alkanediyl group; most preferably, wherein each $R^5$ is a —$CH_2$— group); wherein $R^6$ and $R^7$ are independently selected from the group consisting of a $C_{1-6}$ alkanediyl group (preferably, wherein $R^6$ and $R^7$ are independently selected from the group consisting of a $C_{1-4}$ alkanediyl group; more preferably, wherein $R^6$ and $R^7$ are independently selected from the group consisting of a $C_{1-3}$ alkanediyl group; most preferably, a —$CH_2CH_2$— group)(preferably, wherein $R^6$ and $R^7$ are the same); wherein each $R^8$ is selected from the group consisting of a hydrogen and a $C_{1-4}$ alkyl group (preferably, wherein $R^8$ is a hydrogen); wherein each $R^9$ is independently selected from a $C_{1-22}$ alkyl group (preferably, a $C_{6-22}$ alkyl group; more preferably, a $C_{6-18}$ alkyl group; most preferably, a $C_{8-16}$ alkyl group) and wherein each $R^{10}$ is independently selected from the group consisting of a methyl group and an ethyl group (preferably, a methyl group). Most preferably, the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected to impart thermal protection to hair from exposure to heat and wherein the heat protectant is selected to be a functionalized dextran polymer, comprising a dextran polymer functionalized with moieties selected from the group consisting of (a) tertiary amine groups of formula A; (b) quaternary ammonium crosslinking groups of formula B; (c) quaternary ammonium groups of formula E; and (d) combinations thereof; wherein the quaternary ammonium crosslinking groups of formula B are selected from the group consisting of

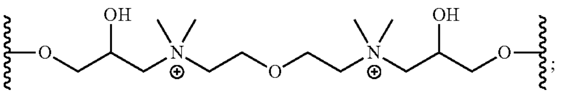

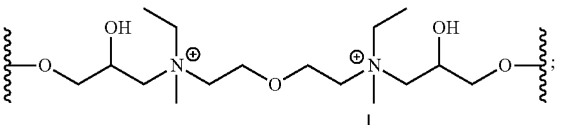

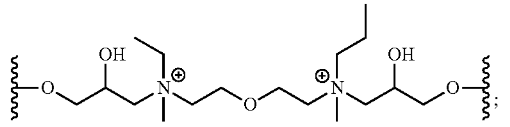

and

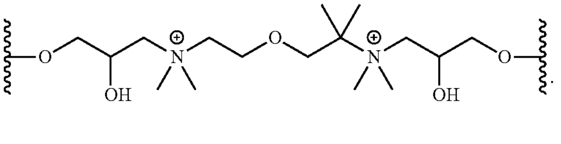

Preferably, the heat protectant has a Kjeldahl nitrogen content corrected for ash and volatiles, TKN, of 0.4 to 5.0 wt % (preferably, 0.5 to 4.5 wt %; more preferably, 0.5 to 4.0 wt %; most preferably, 0.5 to 3.5 wt %) (measured using a Buchi KjelMaster K-375 automated analyzer, corrected for volatiles and ash measured as described in ASTM method D-2364).

Preferably, the heat protectant comprises<0.001 meg/gram (preferably, <0.0001 meq/gram; more preferably, <0.00001 meq/gram; most preferably, <detectable limit) of aldehyde functionality.

Preferably, the heat protectant comprises<0.1% (preferably, <0.01%; more preferably, <0.001%; most preferably, <detectable limit), of the linkages between individual glucose units in the deposition aid polymer are ß-1,4 linkages.

Preferably, the heat protectant comprises<0.1% (preferably, <0.01%; more preferably, <0.001%; most preferably, <detectable limit), of the linkages between individual glucose units in the deposition aid polymer are ß-1,3 linkages.

Preferably, the heat protectant comprises<0.001 meq/gram (preferably, <0.0001 meq/gram; more preferably, <0.00001 meq/gram; most preferably, <detectable limit) of silicone containing functionality.

Preferably, the aqueous thermal protectant formulation prepared and used in the process of the present invention is selected from the group consisting of a rinse off hair treatment and a leave on hair treatment. More preferably, the aqueous thermal protectant formulation prepared and used in the process of the present invention is a leave on hair treatment.

Preferably, the aqueous thermal protectant formulation prepared and used in the process of the present invention, optionally, further comprises at least one additional ingredient selected from the group consisting of a cosmetically acceptable cleansing surfactant; a thickener (e.g., polysaccharides, cellulosic polymers); a soap; a colorant; a pH adjusting agent; an antioxidant (e.g., butylated hydroxytoluene); an emollient (polyoxyethylene glycol ($C_{7-20}$) fatty acid, esters of glycerol—e.g., PEG-7 glyceryl cocoate, PEG-30 glyceryl cocoate, PEG-12 glyceryl laureate, PEG-20 glyceryl oleate); a wax; a foaming agent; an emulsifying agent (e.g. PEG-100 stearate & glyceryl stearate mixture); a colorant; a fragrance; a chelating agent (e.g., disodium EDTA, tetrasodium EDTA, citric acid, lactic acid); an antimicrobial agent/preservative (e.g., methylchloroisothiazolinone, phenoxyethanol, methylisothiazolinone, esters of parabenzoic acid, diazolidinyl urea and imidazolidinyl urea, benzoic acid, sorbic acid); a bleaching agent; a lubricating agent; a sensory modifier; a sunscreen additive; a vitamin; a protein/amino acid; a plant extract; a natural ingredient; a bioactive agent; an anti-aging agent; a pigment; an acid; a penetrant; an anti-static agent; an anti-frizz agent; an anti-dandruff agent; a hair waving/straightening agent; a hair styling agent; a hair oil; an absorbent; a hard particle; a soft particle; a conditioning agent (e.g., guar hydroxypropyltrimonium chloride, PQ-10, PQ-7); a slip agent; an opacifier; a pearlizing agent and a salt. More preferably, the aqueous thermal protectant formulation prepared and used in the process of the present invention, optionally, further comprises at least one additional ingredient selected from the group consisting of an emulsifying agent (e.g. PEG-100 stearate & glyceryl stearate mixture); an antimicrobial agent/preservative (e.g., methylchloroisothiazolinone, phenoxyethanol, methylisothiazolinone, esters of parabenzoic acid, diazolidinyl urea and imidazolidinyl urea, benzoic acid, sorbic acid); a thickener (e.g., polysaccharides, cellulosic polymers); and a chelating agent (e.g., disodium EDTA, tetrasodium EDTA, citric acid, lactic acid). Most preferably, the aqueous thermal protectant formulation prepared and used in the process of the present invention, optionally, further comprises at least one additional ingredient selected from the group consisting of an emulsifying agent mixture of PEG-100 stearate & glyceryl stearate mixture; a hydroxyethyl cellulose polymer thickener; cetearyl alcohol emollient; tetrasodium ethylene diamine tetraacetic acid chelating agent and a mixture of phenoxyethanol and methylisothiazolinone preservative.

Preferably, the aqueous thermal protectant formulation prepared and used in the process of the present invention, optionally further comprises an emulsifying agent. More preferably, the aqueous thermal protectant formulation prepared and used in the process of the present invention further comprises 0.01 to 80 wt % (more preferably, 0.1 to 5 wt %; still more preferably, 0.5 to 2 wt %, most preferably, 0.75 to 1.25 wt %), based on weight of the aqueous thermal protectant formulation, of an emulsifying agent. Most preferably, the aqueous thermal protectant formulation prepared and used in the process of the present invention further comprises 0.01 to 80 wt % (more preferably, 0.1 to 5 wt %; still more preferably, 0.5 to 2 wt %, most preferably, 0.75 to 1.25 wt %), based on weight of the aqueous thermal protectant formulation, of an emulsifying agent; wherein the aqueous conditioner formulation is selected from the group consisting of a leave on hair conditioner and a rinse off hair conditioner; and wherein the emulsifying agent comprises a mixture of PET-100 stearate and glyceryl stearate.

Preferably, the aqueous thermal protectant formulation prepared and used in the process of the present invention optionally further comprises a thickener. More preferably, the aqueous thermal protectant formulation prepared and used in the process of the present invention further comprises a thickener, wherein the thickener is selected to increase the viscosity of the aqueous conditioner formulation, preferably without substantially modifying the other properties of the personal care composition. Still more preferably, the aqueous thermal protectant formulation prepared and used in the process of the present invention further comprises a thickener, wherein the thickener is selected to increase the viscosity of the personal care composition, preferably without substantially modifying the other properties of the personal care composition and wherein the thickener accounts for 0 to 5.0 wt % (preferably, 0.1 to 5.0 wt %; more preferably, 0.2 to 2.5 wt %; most preferably, 0.5 to 2.0 wt %), based on weight of the aqueous thermal protectant formulation. Preferred thickeners include polysaccharides and cellulosic polymers. Preferably, the thickener is a hydroxyethyl cellulose polymer.

Preferably, the aqueous thermal protectant formulation prepared and used in the process of the present invention optionally further comprises a chelating agent. More preferably, the aqueous thermal protectant formulation prepared and used in the process of the present invention further comprises 0.001 to 0.75 wt % (preferably, 0.03 to 0.25 wt %), based on weight of the aqueous thermal protectant formulation, of a chelating agent, wherein the chelating agent is selected from the group consisting of disodium ethylenediaminetetraacetic acid (EDTA), tetrasodium EDTA, citric acid, lactic acid and mixtures thereof. Most preferably, the aqueous thermal protectant formulation prepared and used in the process of the present invention further comprises 0.001 to 0.75 wt % (preferably, 0.03 to 0.25 wt %), based on weight of the aqueous thermal protectant formulation, of a chelating agent, wherein the chelating agent, wherein the chelating agent includes tetrasodium EDTA.

Preferably, the aqueous thermal protectant formulation prepared and used in the process of the present invention optionally further comprises an antimicrobial agent/preservative. More preferably, the aqueous thermal protectant formulation prepared and used in the process of the present invention further comprises 0.05 to 1.25 wt % (preferably, 0.1 to 1 wt %; more preferably, 0.25 to 0.75 wt %), based on weight of the aqueous thermal protectant formulation, of an antimicrobial agent/preservative; wherein the antimicrobial/preservative is selected from the group consisting of phenoxyethanol, benzoic acid, benzyl alcohol, sodium benzoate, DMDM hydantoin, 2-ethylhexyl glyceryl ether, isothiazolinone (e.g., methylchloroisothiazolinone, methylisothiazolinone) and mixtures thereof. Most preferably, the aqueous thermal protectant formulation prepared and used in the process of the present invention optionally further comprises 0.05 to 1.25 wt % (preferably, 0.1 to 1 wt %; more preferably, 0.25 to 0.75 wt %), based on weight of the aqueous thermal protectant formulation, of an antimicrobial agent/preservative; wherein the antimicrobial/preservative is a mixture of phenoxyethanol and an isothiazolinone (more preferably, wherein the antimicrobial/preservative is a mixture of phenoxyethanol and methylisothiazolinone).

Preferably, the aqueous thermal protectant formulation prepared and used in the process of the present invention contains<detectable limit of monosaccharide having amine groups.

Preferably, the aqueous thermal protectant formulation prepared and used in the process of the present invention contains<detectable limit of sugar.

Preferably, the aqueous thermal protectant formulation prepared and used in the process of the present invention contains<detectable limit of soy protein.

Preferably, the aqueous thermal protectant formulation prepared and used in the process of the present invention contains<detectable limit of hydrolyzed silk.

Preferably, in the process for reducing hair (preferably, mammalian hair; more preferably, human hair) damage upon exposure of the hair to heat of the present invention, the provided heat protectant formulation, the cosmetically acceptable aqueous carrier and any additional ingredients are combined using known processing techniques to provide the aqueous thermal protectant formulation. More preferably, in the process for reducing hair (preferably, mammalian hair; more preferably, human hair) damage upon exposure of the hair to heat of the present invention, the provided heat protectant formulation, the cosmetically acceptable aqueous carrier and any additional ingredients are combined using known processing techniques to provide the aqueous thermal protectant formulation; wherein the aqueous thermal protectant formulation comprises 25 to 99.95 wt % (preferably, 50 to 99.9 wt %; more preferably, 75 to 99.5 wt %; most preferably, 80 to 99.3 wt %), based on weight of the aqueous thermal protectant formulation, of the cosmetically acceptable aqueous carrier; and 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of the heat protectant.

Preferably, in the process for reducing hair (preferably, mammalian hair; more preferably, human hair) damage upon exposure of the hair to heat of the present invention, the aqueous thermal protectant formulation is applied to the hair using well known techniques. More preferably, in the process for reducing hair (preferably, mammalian hair; more preferably, human hair) damage upon exposure of the hair to heat of the present invention, the aqueous thermal protectant formulation is applied to the hair, wherein 0.01 g to 5 g of the aqueous thermal protectant formulation is applied per g of hair.

Preferably, in the process for reducing hair (preferably, mammalian hair; more preferably, human hair) damage upon exposure of the hair to heat of the present invention, comprises providing a heat generating hair care appliance. Heat generating hair care appliances typically fall into one of two major categories, namely (1) heat generating hair care appliances that are used preferably on wet hair (e.g., hair dryer) and (2) heat generating hair care appliances used preferably on dry hair (e.g., flat ironing/curling; hat rollers).

Heat generating appliances that are designed for and typically used on wet hair are sometimes referred to as hot air hair care appliances. Examples of hot air hair care appliances include hair dryers and hot air hair stylers. The typical hair dryer is designed to direct hot air towards the hair to facilitate drying of the hair. In these hair dryers, the air is directed through appropriate orifices and accelerated by a fan. The air expelled by such hair dryers may be heated, but example, through use of a resistive heater. Hair dryers may incorporate a hood, wherein a major portion of the hair is covered by the hood. Hair dryers typically operate by delivering hot air temperatures of 50 to 100 °C Hot air stylers typically direct hot air through an attachment designed for combing or otherwise manipulating the hair. Hot air stylers may deliver hot air temperatures of up to 130° C.

Heat generating appliances that are designed for and typically used on dry hare are sometimes referred to as hot surface hair care appliances. Examples of hot surface hair care appliances may be designed for hair curling and/or hair straightening. Hot surface hair care appliances typically rely on resistive heating wherein heat is transported to the hair via direct contact with the appliance rather than using hot air. The heat transfer is typically effectuated by bringing the hair into contact with a metallic or ceramic surface of the hot surface hair care appliance. Hot surface hair care appliances are typically not used to dry the hair. Rather, hot surface hair care appliances are implemented to change the style of the hair, typically either to produce curls in the hair or to straighten the hair. The surfaces of hot surface hair care appliances designed to contact and transfer heat to hair typically achieve temperatures of 130 to 300° C.

Preferably, in the process for reducing hair (preferably, mammal hair; more preferably, human hair) damage upon exposure of the hair to heat of the present invention, comprises exposing the hair to heat at a temperature of 50 to 300 °C (preferably, 80 to 280 °C; more preferably, 90 to 275 °C; most preferably, 100 to 250 °C) using the heat generating hair care appliance (wherein the heat generating hair care appliance is selected from the group consisting of at least one of a hot air hair care appliance (e.g., hair dryer, hot air hair styler) and a hot surface hair care appliance (e.g., hot curlers, flat iron and a curling iron)) (e.g., for drying or styling hair). More preferably, in the process for reducing hair (preferably, mammal hair; more preferably, human hair) damage upon exposure of the hair to heat of the present invention, comprises exposing the hair to heat at a temperature of 50 to 300 °C (preferably, 80 to 280 °C; more preferably, 90 to 275 °C; most preferably, 100 to 250 °C) using the heat generating hair care appliance (wherein the heat generating hair care appliance is selected from the group consisting of at least one of a hot air hair care appliance (e.g., hair dryer, hot air hair styler) and a hot surface hair care appliance (e.g., hot curlers, flat iron and a curling iron)) for 1 to 40 minutes (e.g., for drying or styling hair). Most preferably, in the process for reducing hair (preferably, mammal hair; more preferably, human hair) damage upon exposure of the hair to heat of the present invention, comprises exposing the hair to heat at a temperature of 50 to 300 °C (preferably, 80 to 280 °C; more preferably, 90 to 275 °C; most preferably, 100 to 250 °C) using the heat generating hair care appliance (wherein the heat generating hair care appliance is selected from the group consisting of at least one of a hot air hair care appliance (e.g., hair dryer, hot air hair styler) and a hot surface hair care appliance (e.g., hot curlers, flat iron and a curling iron)) for 2 to 40 minutes (e.g., for drying or styling hair); wherein the hair is exposed to heat using a hot air hair care appliance for 1 to 20 minutes for drying the hair; and then wherein the hair is exposed to heat using a hot surface hair care appliance for 1 to 20 minutes for styling the hair.

Preferably, in the process for reducing hair (preferably, mammalian hair; more preferably, human hair) damage upon exposure of the hair to heat of the present invention, optionally further comprises rinsing the hair with water. More preferably, in the process for reducing hair (preferably, mammalian hair; more preferably, human hair) damage upon exposure of the hair to heat of the present invention, optionally further comprises rinsing the hair with water before applying the aqueous protectant formulation to the hair (preferably, wherein the hair is rinsed with water 30 seconds to 20 minutes (more preferably, 30 seconds to 5 minutes)). Most preferably, in the process for reducing hair (preferably, mammalian hair; more preferably, human hair) damage upon exposure of the hair to heat of the present invention, optionally further comprises rinsing the hair with water before applying the aqueous thermal protectant formulation to the hair (preferably, wherein the hair is rinsed with water 30 seconds to 20 minutes (more preferably, 30 seconds to 5 minutes)); and then drying the rinsed hair by at least one of toweling and pressing the hair to remove excess water before applying the aqueous protectant formulation to the hair.

Preferably, in the process for reducing hair (preferably, mammalian hair; more preferably, human hair) damage upon exposure of the hair to heat of the present invention, optionally further comprises at least one of combing and brushing the hair. More preferably, in the process for reducing hair (preferably, mammalian hair; more preferably, human hair) damage upon exposure of the hair to heat of the present invention, optionally further comprises at least one of combing and brushing the hair after application of the aqueous thermal protectant formulation (preferably, wherein the hair is combed and/or brushed before, during and/or after exposing the hair to heat from the heat generating hair care appliance).

Some embodiments of the present invention will now be described in detail in the following Examples.

Synthesis S1: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran polymer (25.0 g; Aldrich, catalog number D4876). The addition funnel was charged with a 70% aqueous solution of 2,3-epoxypropyltrimethylammonium chloride (30.0 g; QUAB® 151 available from SKW QUAB Chemicals) and a 40% aqueous solution of 3-chloro-2-hydroxypropyl-1-dimethyldodecylammonium chloride (39.3 g; QUAB® 342 available from SKW QUAB Chemicals). While stirring, the head space in the flask was purged with a slow, steady flow of nitrogen (about one bubble per second) for one hour to remove any entrained oxygen in the apparatus.

While stirring under nitrogen a 25% aqueous sodium hydroxide solution (11.0 g) was added to the flask contents dropwise using a plastic syringe over 2 minutes. After stirring for an hour under the nitrogen purge, the contents of the addition funnel were added to the contents of the flask over three minutes. The flask contents were then stirred under nitrogen for 20 minutes before applying heat to the mantle with a set point temperature of 55 °C. The flask contents were then heated with continued stirring under nitrogen for 1.5 hours.

The flask contents were then cooled in a water bath while maintaining a positive nitrogen pressure in the flask. The flask contents were neutralized by adding 1.66 g of glacial acetic acid with continued stirring for 10 minutes under nitrogen.

The product polymer was recovered by non-solvent precipitation in methanol; roughly 1 L of methanol was used for the precipitation of the entire 25.0 g batch. The methanol was decanted off and the polymer was placed in a dish to be dried in vacuo at 50° C overnight. The dried polymer was manually ground with a mortar and pestle, and screened through a US standard #30 sieve.

The product polymer was obtained as a white solid (27.2 g), with a volatiles content of 5.13%, and ash content (as sodium chloride) of 0.56%, and a Kjeldahl nitrogen content (corrected for ash and volatiles) of 1.329%, corresponding to a total cationic substitution, CS, value of 0.134.

Synthesis S2: Synthesis of Dextran Crosslinking Agent

Bis[2-(N,N-dimethyamino)ethyl]ether (10.84 g) and water (23.12 g) were mixed together in a container. The pH of the container contents was adjusted to 8.5 with concentrated hydrochloric acid. The set point temperature for the container contents was maintained at 25 °C while 99.9% epichlorohydrin (20.84 g) was added to the container over a period of 60 minutes. The set point temperature of the container contents was maintained at 25 °C for an additional 2 hours, before raising the set point temperature to 50 °C and maintaining that temperature set point for 2 hours. The pH of the container contents was then lowered to <2.0 with concentrated hydrochloric acid and the set point temperature was increased to 70 °C and maintaining that temperature set point for an hour. The container contents were then cooled. After the temperature of the container contents fell below 50 °C, the pH of the container contents was adjusted to 4-6 with 50% sodium hydroxide solution. An extraction of the container contents was then performed with methylene chloride seven times (1 vol: 1 vol), then the residual methylene chloride was removed conventionally. The recovered material contained 39.4 wt % product solids. The product solids were analyzed via $^{13}C$ NMR to confirm the product was

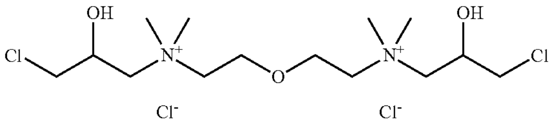 [SMILES: C[N+](C)(CCOCC[N+](C)(C)CC(O)CCl)CC(O)CCl ; [Cl-] ; [Cl-]]

N,N'-(oxybis(ethane-2,1-diyl))bis(3-chloro-2-hydroxy-N,N-dimethylpropan-1-aminium) chloride.

Synthesis S3: Synthesis of Crosslinked Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran (23.23 g; Aldrich product #D4876) and deionized water (120 g). While the contents were stirring, the apparatus was purged with nitrogen to displace any oxygen entrained in the system. The nitrogen flow rate was about 1 bubble per second. The mixture was purged with nitrogen while stirring for one hour. Using a plastic syringe, a 50% aqueous sodium hydroxide solution (14.9 g) was added over a period of a few minutes to the flask contents with stirring under nitrogen. The flask contents were then allowed to stir under nitrogen for 30 minutes. Then a 47% aqueous solution of a dextran crosslinking agent prepared according to Synthesis S2 (74.45 g) was added to the flask contents and allowed to stir for five minutes prior to heating. Then heat was applied to the flask contents with a heating mantle controlled using the J-KEM controller set at 55 °C. The flask contents were heated to and maintained at 55 °C for 90 minutes. The flask contents were then cooled to room temperature while maintaining a positive nitrogen pressure in the flask. When the flask contents reached room temperature, the flask contents were neutralized by adding glacial acetic acid (3.0 g) and the flask contents were allowed to stir for ten minutes. The flask contents were then diluted and transferred without purification for use; the diluted product solids content was 11.1 wt %. An aliquot of the solution was precipitated from methanol and dried in vacuo at 50 °C. The total Kjeldahl nitrogen content, TKN, of the dried precipitate was measured using a Buchi KjelMaster K-375 automated analyzer at 2.72 wt %.

Synthesis S4: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran polymer (126.92 g; 21.4% Polydex aqueous dextran), N,N-dimethyldodecylamine (13.54 g) and epichlorohydrin (5.84 g). The contents of the flask were stirred at 70 rpm. While stirring, the head space in the flask was purged with a slow, steady flow of nitrogen (about one bubble per second) for one hour to remove any entrained oxygen in the apparatus.

After the one hour nitrogen purge, heat was applied to the flask contents using a heating mantle and the J-KEM controller (set-point of 70 °C). While stirring under nitrogen, the flask contents were maintained at 70 °C for 5 hours. During this time, the color of the flask contents changed from yellow to dark brown, and the viscosity noticeably increased as the reaction progressed.

The flask contents were then cooled in a water bath while maintaining a positive nitrogen pressure in the flask. A solid polymer product was recovered from the flask contents by non-solvent precipitation with acetone. A Waring blender was charged with 500 mL of acetone and approximately 20 mL of polymer solution was slowly and continuously added at moderate mixing speed using a plastic disposable syringe. The polymer was recovered by vacuum filtration through a Buchner funnel with a fine frit. The Waring blender was charged with fresh acetone and the non-solvent precipitation of the remaining aqueous solution was continued. The polymer was briefly air dried, then dried overnight in vacuo at 50 °C. The dried polymer was manually ground with a mortar and pestle, and screened through a US standard #30 sieve.

The product polymer was obtained as a white solid (29.96 g), with a volatiles content of 2.35%, and ash content (as sodium chloride) of 1.99%, and a Kjeldahl nitrogen content was measured using a Buchi KjelMaster K-375 automated analyzer (corrected for ash and volatiles) of 1.079%, corresponding to a CS value of 0.163.

Synthesis S5: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran polymer (29.42 g; Aldrich, catalog number D4876); deionized water (100.69 g); N,N-dimethylhexadecylamine (17.10 g) and epichlorohydrin (5.83 g). The contents of the flask were stirred at 70 rpm. While stirring, the head space in the flask was purged with a slow, steady flow of nitrogen (about one bubble per second) for one hour to remove any entrained oxygen in the apparatus.

After the one hour nitrogen purge, heat was applied to the flask contents using a heating mantle and the J-KEM controller (set-point of 70 °C). While stirring under nitrogen, the flask contents were maintained at 70 °C for 5 hours. During this time, the viscosity of the flask contents noticeably increased as the reaction progressed.

The flask contents were then cooled in a water bath while maintaining a positive nitrogen pressure in the flask. A solid polymer product was recovered from the flask contents by non-solvent precipitation with acetone. A Waring blender was charged with 500 mL of methanol and approximately 20 mL of polymer solution was slowly and continuously added at moderate mixing speed using a plastic disposable syringe. The polymer was recovered by vacuum filtration through a Buchner funnel with a fine frit. The Waring blender was charged with fresh methanol and the non-solvent precipitation of the remaining aqueous solution was continued. The polymer was briefly air dried, then dried overnight in vacuo at 50 °C. The dried polymer was manually ground with a mortar and pestle, and screened through a US standard #30 sieve.

The product polymer was obtained as a white solid (21.66 g), with a volatiles content of 2.91%, and ash content (as sodium chloride) of 0.20%, and a Kjeldahl nitrogen content was measured using a Buchi KjelMaster K-375 automated analyzer (corrected for ash and volatiles) of 0.543%, corresponding to a CS value of 0.073.

Comparative Examples C1-C7 and Examples 1-5: Thermal Protection

Heat Damage Procedure

Hair tresses (2 g, Medium Brown Virgin Hair available from International Hair Importers) were wetted for 30 seconds in 40 °C distilled water, then a 9 wt % sodium lauryl sulfate (SLS) solution (0.2 g/g of hair) was massaged into the hair before rinsing with water flowing at 0.4 L/min for 60 seconds; detangled with a brush. The hair tresses where then treated by applying and massaging into the tress for 1 minute, an aqueous protectant solution as noted in Table 1 (if any) at an application rate of 0.15 g/g or hair. The tresses were allowed to air dry at least 12 hours at room temperature (25 °C) and 50% relative humidity prior to the heat treatment. Before the heat treatment of the hair tresses, a flat iron (Sexy Hair Smooth Lock Pro Ceramic Flat Iron) was preheated to 232 °C. Then the tresses were treated ten times for ten seconds each with the flat iron from root to tip. This process of washing the hair tresses, treating the hair tresses with 1 wt % aqueous protectant solution and heat treatment was repeated three times with each hair tress before performance evaluation. After the third heat treatment cycle, the tresses were washed with 9 wt % SLS solution (0.2 g/g hair) for 30 seconds, rinsed with water for 60 seconds and dried overnight at 25 °C and 50% relative humidity before performing the DSC studies below.

TABLE 1

| Example | Protectant Solution |
|---|---|
| Comp. Ex. C1 | No protectant solution/no heat treatment |
| Comp. Ex. C2 | No protectant solution |
| Comp. Ex. C3 | 3% aq. soln. of Amodimethicone (and) citrimonium chloride (and) trideceth-3 (and) trideceth-15[a] |
| Comp. Ex. C4 | 3% aq. soln. of Bis-diisopropanolamino-PG-propyl dimethicone/bis-isobutyl PEG-14 copolymer (and) polysorbate 20 (and) butyloctanol[b] |
| Comp. Ex. C5 | 1% aq. soln. of Guar hydroxypropyltrimonium chloride[c] |
| Comp. Ex. C6 | 1% aq. soln. of Hydroxyethyl cellulose[d] |
| Comp. Ex. C7 | 1% aq. soln. of Dextran[e] |
| Example 1 | 1% aq. soln. of polymer from Synthesis S1 |
| Example 2 | 1% aq. soln. of DEAE Dextran[f] |
| Example 3 | 1% aq. soln. of polymer from Synthesis S3 |
| Example 4 | 1% aq. soln. of polymer from Synthesis S4 |
| Example 5 | 1% aq. soln. of polymer from Synthesis S5 |

[a]available from The Dow Chemical Company under tradename DOWSIL ™ 969 emulsion
[b]available from The Dow Chemical Company under tradename DOWSIL ™ CE-8411 smooth plus emulsion
[c]available from Solvay Novecare under tradename JAGUAR Excel
[d]available from The Dow Chemical Company under tradename CELLOCIZE ™ PCG-10 hydroxyethyl cellulose
[e]available from Sigma Aldrich under catalog number D4876
[f]available from Sigma Aldrich under catalog number D9885.

DSC Studies

Samples were prepared from the hair tresses treated according to each of Comparative Examples C1-C7 and Examples 1-5 by isolating at least two different locks of hair from each tress and trimming them into small (<2 mm long) pieces using clippers. The entire length of the chosen hair locks was cut up and randomly distributed on weighing paper to average any difference in hair properties along the length of the tress. A 10 mg sample was then taken from each pile of small hair pieces using a tweezers. The samples were placed into separate 40 μL stainless steel pan (Perkin-Elmer part number 0319-0218) and distributed evenly on the bottom of the pan. To each pan was added 30 μL of deionized water using a pipette, which plasticizes the cuticle and lowers the hair denaturation temperature below the decomposition temperature. The pans were then press-sealed with a Viton O-ring and a stainless steel lid and weight for total starting mass. To allow the hair samples to equilibrate in hydration level, the sealed pans were allowed to sit for 12 hours at 25 °C. The hair samples were then analyzed by a Differential Scanning calorimeter (DSC) paired with a Refrigerated Cooling System (RCS90) unit. The hair samples were analyzed by equilibrating at 40 °C then heating the samples to 200 °C at a 10 °C per minute temperature ramp rate. During the analysis, the cell flow rate was 25 mL per minute of nitrogen. Instrumental software (TRIOS) was used to determine both the denaturation temperature and the denaturation enthalpy. The denaturation temperature was determined as the peak temperature of the endothermic transition and the denaturation enthalpy was determined by integrating the endothermic transition. The peak temperature from the respect of DSC curves are reported in Table 2. The denaturation enthalpy for the hair samples are also reported in Table 2.

TABLE 2

| Example | Peak Temp. (°C) | Enthalpy (J/g) |
|---|---|---|
| Comp. Ex. C1 (No protectant/no heat damage) | 152.6 | 22 |
| Comp. Ex. C2 (No protectant/heat damage) | 142.0 | 13 |
| Comp. Ex. C3 | 149.2 | 17 |
| Comp. Ex. C4 | 148.7 | 17 |
| Comp. Ex. C5 | 147.5 | 17 |
| Comp. Ex. C6 | 147.6 | 17 |
| Comp. Ex. C7 | 148.3 | 17 |
| Example 1 | 149.8 | 19 |
| Example 2 | 149.7 | 20 |
| Example 3 | 149.4 | 19 |
| Example 4 | 149.6 | 19 |
| Example 5 | 149.7 | 18 |

We claim:

1. A process for reducing hair damage upon exposure of the hair to heat, comprising:

providing a cosmetically acceptable aqueous carrier;

selecting a heat protectant, wherein the heat protectant is selected based on its ability to impart thermal protection to hair from exposure to heat, wherein the heat protectant is selected to be a functionalized dextran polymer, comprising a dextran polymer functionalized with moieties of formula D (D)

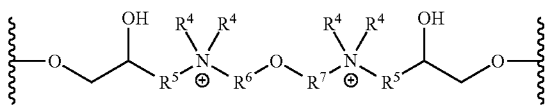

wherein

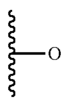

is a pendant oxygen on the dextran polymer; wherein each $R^4$ is independently selected from a substituted or unsubstituted $C_{1-6}$ alkyl group; wherein each $R^5$ is independently selected from the group consisting of a $C_{1-6}$ alkanediyl group; and wherein $R^6$ and $R^7$ are independently selected from the group consisting of a $C_{1-6}$ alkanediyl group;

providing the selected heat protectant;

combining the cosmetically acceptable aqueous carrier and the heat protectant to form an aqueous thermal protectant formulation, wherein the aqueous thermal protectant formulation comprises 0.1 to 5 wt %, based on weight of the aqueous thermal protectant formulation, of a heat protectant;

providing a hair;

applying the aqueous thermal protectant formulation to the hair to provide protected hair;

providing a heat generating hair care appliance; and exposing the protected hair to a temperature of 50 to 300 °C using the heat generating hair care appliance for 1 to 30 minutes.

2. The process of claim 1, wherein the dextran polymer has a weight average molecular weight of 50,000 to 3,000,000 Daltons and wherein the dextran polymer is a branched chain dextran polymer comprising a plurality of glucose structural units; wherein 90 to 98 mol % of the glucose structural units are connected by α-D-1,6 linkages and 2 to 10 mol % of the glucose structural units are connected by α-1,3 linkages.

3. The process of claim 1, wherein the quaternary ammonium crosslinking groups of formula D are selected from the group consisting of

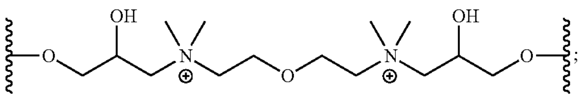
;

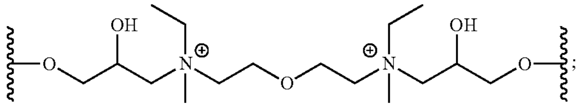
;

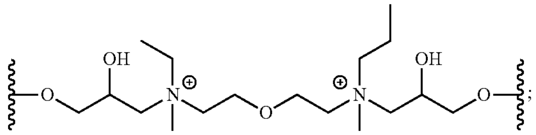
; and

-continued

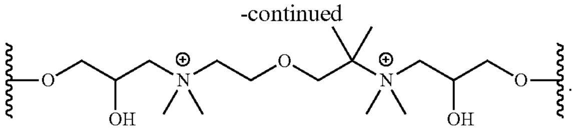
.

4. The process of claim 1, wherein the aqueous thermal protectant formulation formed contains 0.15 to 2.5 wt % based on weight of the aqueous thermal protectant formulation, of the heat protectant.

5. The process of claim 4, wherein the protected hair to which the aqueous protectant formulation has been applied exhibits a higher denaturation temperature than hair similarly exposed to heat but without application of the aqueous protectant formulation.

6. The process of claim 5, wherein the protected hair to which the aqueous protectant formulation has been applied exhibits a higher denaturation enthalpy than hair similarly exposed to heat but without application of the aqueous protectant formulation.

7. The process of claim 6, further comprising: rinsing the hair with water before applying the aqueous thermal protectant formulation to the hair.

8. The process of claim 7, further comprising: drying the rinsed hair by at least one of toweling and pressing hair to remove excess water before applying the aqueous thermal protectant formulation to the hair.

9. The process of claim 8, further comprising: at least one of combing and brushing the protected hair following application of the aqueous thermal protectant formulation.

10. The process of claim 1, wherein the aqueous protectant formulation applied to the hair, further comprises a thickener.

11. The process of claim 1, wherein the aqueous protectant formulation, further comprises an additive selected from the group consisting of a thickener, a chelating agent, a preservative, an emollient, a cosmetically acceptable cleansing surfactant and mixtures thereof.

* * * * *